US00PP34111P2

(12) United States Plant Patent
Grazzini

(10) Patent No.: US PP34,111 P2
(45) Date of Patent: Apr. 5, 2022

(54) ***SOLENOSTEMON* PLANT NAMED 'G18152'**

(50) Latin Name: *Solenostemon scutellarioides*
Varietal Denomination: G18152

(71) Applicant: Richard A. Grazzini, Bellefonte, PA (US)

(72) Inventor: Richard A. Grazzini, Bellefonte, PA (US)

(73) Assignee: GardenGenetics LLC, Bellefonte, PA (US)

( * ) Notice: Subject to any disclaimer, the term of this patent is extended or adjusted under 35 U.S.C. 154(b) by 0 days.

(21) Appl. No.: 17/372,086

(22) Filed: Jul. 9, 2021

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./373, 263.1, 469
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Solenostemon* plant named 'G18152', characterized by its compact, upright to slightly outwardly spreading plant habit; moderately vigorous growth habit; freely branching habit; dense appearance; very dark purple-colored stems and leaves; and good garden performance.

1 Drawing Sheet

Botanical designation: *Solenostemon scutellarioides.*
Cultivar denomination: 'G18152'.

BACKGROUND OF THE INVENTION

The present invention relates to a new and distinct cultivar of *Solenostemon* plant, botanically known as *Solenostemon scutellarioides*, commonly referred to as Coleus, and hereinafter referred to by the name 'G18152'.

The new *Solenostemon* plant originated from a cross-pollination in September, 2017 in Bellefonte, Pa. of an unidentified proprietary selection of *Solenostemon scutellarioides*, not patented, as the female, or seed, parent, with a mixture of dark-leafed unidentified proprietary selections of *Solenostemon scutellarioides*, not patented, as the male, or pollen, parent. The new *Solenostemon* plant was discovered and selected by the Inventor as a single flowering plant within the progeny of the stated cross-pollination in a controlled greenhouse environment in Bellefonte, Pa. in August, 2018.

Asexual reproduction of the new *Solenostemon* plant by vegetative terminal cuttings in a controlled greenhouse environment in Bellefonte, Pa. since August, 2018 has shown that the unique features of this new *Solenostemon* plant are stable and reproduced true to type in successive generations.

SUMMARY OF THE INVENTION

The new *Solenostemon* plant has not been observed under all possible combinations of cultural practices and environmental conditions. The phenotype may vary somewhat with variations in environment and cultural practices such as temperature and light intensity without, however, any variance in genotype.

The following traits have been repeatedly observed and are determined to be the unique characteristics of 'G18152'.

These characteristics in combination distinguish 'G18152' as a new and distinct *Solenostemon* plant:

1. Compact, upright to slightly outwardly spreading plant habit.
2. Moderately vigorous growth habit.
3. Freely branching habit; dense appearance.
4. Very dark purple-colored stems and leaves.
5. Good garden performance.

Plants of the new *Solenostemon* differ primarily from plants of the female parent selection in plant habit as plants of the new *Solenostemon* are more compact and uniform than plants of the female parent selection.

Plants of the new *Solenostemon* can be compared to plants of *Solenostemon scutellarioides* 'ColorBlaze Dark Star', not patented. In side-by-side comparisons plants of the new *Solenostemon* differ from plants of 'ColorBlaze Dark Star' in the following characteristics:

1. Plants of the new *Solenostemon* are more compact than plants of 'ColorBlaze Dark Star'.
2. Plants of the new *Solenostemon* are more freely branching and are denser than plants of 'ColorBlaze Dark Star'.

Plants of the new *Solenostemon* can be compared to plants of *Solenostemon scutellarioides* 'Giant Exhibition Palisandra', not patented. In side-by-side comparisons plants of the new *Solenostemon* differ from plants of 'Giant Exhibition Palisandra' in the following characteristics:

1. Plants of the new *Solenostemon* are more compact than plants of 'Giant Exhibition Palisandra'.
2. Plants of the new *Solenostemon* are more freely branching and are denser than plants of 'Giant Exhibition Palisandra'.
3. Plants of the new *Solenostemon* have smaller leaves than plants of 'Giant Exhibition Palisandra'.

BRIEF DESCRIPTION OF THE PHOTOGRAPH

The accompanying colored photograph illustrates the overall appearance of the new *Solenostemon* showing the colors as true as it is reasonably possible to obtain in colored reproductions of this type. Colors in the photograph may differ slightly from the color values cited in the detailed botanical description which accurately describe the colors of the new *Solenostemon*.

The photograph is a side perspective view of a typical plant of 'G18152' grown in a container.

DETAILED BOTANICAL DESCRIPTION

The aforementioned photograph and following observations and measurements describe plants grown during the autumn and winter in 10.8-cm containers in a glass-covered greenhouse in Loudon, N.H. and under cultural practices typical of commercial *Solenostemon* production. During the production of the plants, average daily temperatures were 18° C. Plants were grown under long day/short night conditions and were pinched two weeks after planting. Plants were ten weeks from planting when the photographs and description were taken. In the following description, color references are made to The Royal Horticultural Society Colour Chart, 2015 Edition, except where general terms of ordinary dictionary significance are used. Measurements were taken on individual plants.

Botanical classification: *Solenostemon scutellarioides* 'G18152'.

Parentage:

*Female, or seed, parent*.—Unidentified proprietary selection of *Solenostemon scutellarioides*, not patented.

*Male, or pollen, parent*.—Mixture of dark-leafed unidentified proprietary selections of *Solenostemon scutellarioides*, not patented.

Propagation:

*Type*.—By terminal cuttings.

*Time to initiate roots, summer*.—About seven to ten days at soil temperatures about 22° C. and ambient temperatures about 18° C.

*Time to initiate roots, winter*.—About 10 to 14 days at soil temperatures about 22° C. and ambient temperatures about 18° C.

*Time to produce a rooted young plant, summer and winter*.—About five to six weeks at at soil temperatures about 22° C. and ambient temperatures about 18° C.

*Root description*.—Medium in thickness, fibrous; typically white to creamy white in color, actual color of the roots is dependent on substrate composition, water quality, fertilizers, substrate temperature and age of roots.

*Rooting habit*.—Moderately freely branching; medium density.

Plant description:

*Plant and growth habit*.—Compact, upright to slightly outwardly spreading plant habit; moderately vigorous growth habit and moderate growth rate; freely branching habit with lateral branches potentially developing at every node.

*Plant height*.—About 19.5 cm.

*Plant diameter*.—About 24.5 cm.

Lateral branch description:

*Length*.—About 12.5 cm.

*Diameter*.—About 7.5 mm.

*Internode length*.—About 1.5 cm.

*Strength*.—Strong; laterals are flexible.

*Aspect*.—Upright to slightly outwardly spreading.

*Texture and luster*.—Minute and fine pubescence; slightly glossy.

*Color, when developing*.—Close to 146A variably overlain with close to 187A.

*Color, developed*.—Close to 146A variably overlain with close to N186A to N186B.

Leaf description:

*Arrangement*.—Opposite, simple.

*Length*.—About 8.2 cm.

*Width*.—About 5.75 cm.

*Shape*.—Ovate.

*Apex*.—Acute with acuminate tendencies.

*Base*.—Obtuse to cordate.

*Margin*.—Crenate.

*Texture and luster, upper surface*.—Mostly smooth and glabrous with fine and minute pubescence along veins; velvety; rugose; slightly glossy.

*Texture and luster, lower surface*.—Mostly smooth and glabrous with fine and minute pubescence along veins; rugose; matte.

*Venation pattern*.—Pinnate, reticulate.

*Color*.—Developing leaves, upper and lower surfaces: Close to N186B. Fully expanded leaves, upper surface: Close to N186A; venation, close to N186A to N816B. Fully expanded leaves, lower surface: Close to N186B; venation, close to 144A variably overlain with close to N186B.

*Petioles*.—Length: About 1.7 cm. Diameter: About 3 mm. Strength: Strong; flexible. Texture and luster: Minute and fine pubescence; slightly glossy. Color, upper surface: Close to 144A variably overlain with close to N186A to N186B. Color, lower surface: Close to 144A.

Flower description: To date, flower development has not been observed on plants of the new *Solenostemon*.

Pathogen & pest resistance: To date, plants of the new *Solenostemon* have not been observed to be resistant to pests and pathogens common to *Solenostemon* plants.

Garden performance: Plants of the new *Solenostemon* have been observed to tolerate wind, rain, full sunlight and temperatures ranging from 13° C. to 38° C.

It is claimed:

1. A new and distinct *Solenostemon* plant named 'G18152' as illustrated and described.

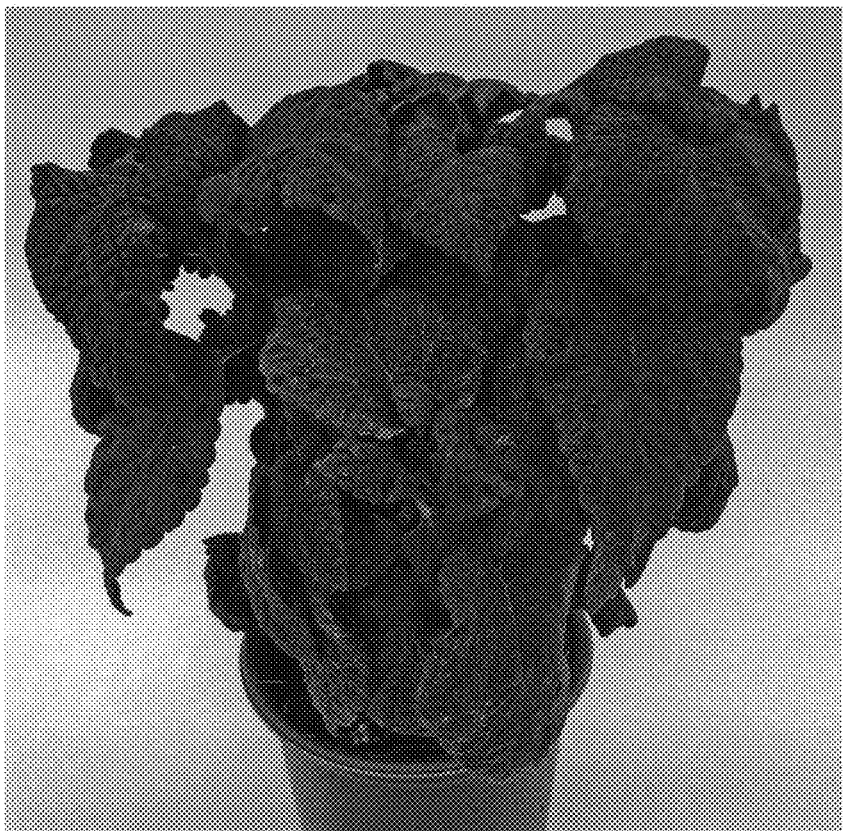

* * * * *